United States Patent
James et al.

(10) Patent No.: US 11,295,853 B2
(45) Date of Patent: Apr. 5, 2022

(54) CARE SUPPORT DEVICE AND METHOD FOR CARE SUPPORT

(71) Applicant: Bode Chemie GmbH, Hamburg (DE)

(72) Inventors: Claudia James, Hamburg (DE); Paolo Marchesini, Ulm (DE); Nicole Witt, Hamburg (DE)

(73) Assignee: Bode Chemie GmbH, Hamburg (DE)

( * ) Notice: Subject to any disclaimer, the term of this patent is extended or adjusted under 35 U.S.C. 154(b) by 793 days.

(21) Appl. No.: 15/740,640

(22) PCT Filed: Jul. 4, 2016

(86) PCT No.: PCT/EP2016/065639
§ 371 (c)(1),
(2) Date: Dec. 28, 2017

(87) PCT Pub. No.: WO2017/001699
PCT Pub. Date: Jan. 5, 2017

(65) Prior Publication Data
US 2018/0197631 A1 Jul. 12, 2018

(30) Foreign Application Priority Data
Jul. 2, 2015 (DE) .......................... 102015212454.1

(51) Int. Cl.
*G16H 40/20* (2018.01)
*G16H 10/60* (2018.01)

(52) U.S. Cl.
CPC ............. *G16H 40/20* (2018.01); *G16H 10/60* (2018.01)

(58) Field of Classification Search
CPC ........ G06Q 30/00; G06Q 50/22; G06Q 30/06; G06Q 10/1097; G06Q 30/02; G06Q 50/01;

(Continued)

(56) References Cited

U.S. PATENT DOCUMENTS 6,839,072 B2   1/2005  Trajkovic et al.
2003/0097060 A1*  5/2003  Yanof et al.
(Continued)

FOREIGN PATENT DOCUMENTS

CN   1606868 A   4/2005
CN   101510257 A   8/2009
(Continued)

OTHER PUBLICATIONS

International Search Report and Written Opinion from PCT/EP2016/065639 dated Oct. 5, 2016 with English Translation of International Search Report provided.

(Continued)

*Primary Examiner* — Michael Tomaszewski
*Assistant Examiner* — William T. Monticello
(74) *Attorney, Agent, or Firm* — Dilworth & Barrese, LLP

(57) ABSTRACT

The invention relates to a care support device (100) characterized by: an image output device (102) which is designed to display symbols (201, . . . , 212; 301, . . . , 312; 401, . . . , 412) which visualize a care procedure; a specification device (103) which is designed to specify symbols to be displayed based on a target care procedure; a detection unit (104) which is designed to detect a user input and to assign displayed symbols to an actual care procedure based on the user input; and an image generation device (105) which is designed to generate symbols which visualize the actual care procedure, wherein the image output device (102) can simultaneously display symbols which visualize the target care procedure and symbols which visualize the actual care procedure.

13 Claims, 5 Drawing Sheets

(58) Field of Classification Search
CPC ........ G06Q 50/00; G06Q 40/00; G06H 10/60;
G06F 19/3418; G06F 17/00; G05B 15/02;
H04R 3/00; H04L 12/2827; G16H 50/30
See application file for complete search history.

(56) References Cited

U.S. PATENT DOCUMENTS

| | | |
|---|---|---|
| 2008/0195128 A1* | 8/2008 | Orbay et al. |
| 2013/0238350 A1* | 9/2013 | Baynham |
| 2014/0022283 A1* | 1/2014 | Chan et al. |
| 2014/0074501 A1 | 3/2014 | Udani |
| 2014/0028549 A1 | 9/2014 | Otsubo et al. |
| 2014/0310595 A1* | 10/2014 | Acharya et al. |
| 2015/0039106 A1* | 2/2015 | Bonstrom et al. |
| 2015/0062157 A1* | 3/2015 | Dragnea |
| 2015/0205916 A1* | 7/2015 | Yamamoto |
| 2015/0305824 A1* | 10/2015 | Yu |
| 2018/0182475 A1* | 6/2018 | Cossler et al. |

FOREIGN PATENT DOCUMENTS

| | | |
|---|---|---|
| CN | 101930498 A | 12/2010 |
| CN | 102831492 A | 12/2012 |
| CN | 103455961 A | 12/2013 |
| DE | 102012101152 A1 | 8/2013 |
| DE | 112012002514 T5 | 3/2014 |
| DE | 112012004902 T5 | 9/2014 |

OTHER PUBLICATIONS

Chinese First Office Action dated Mar. 15, 2021.

\* cited by examiner

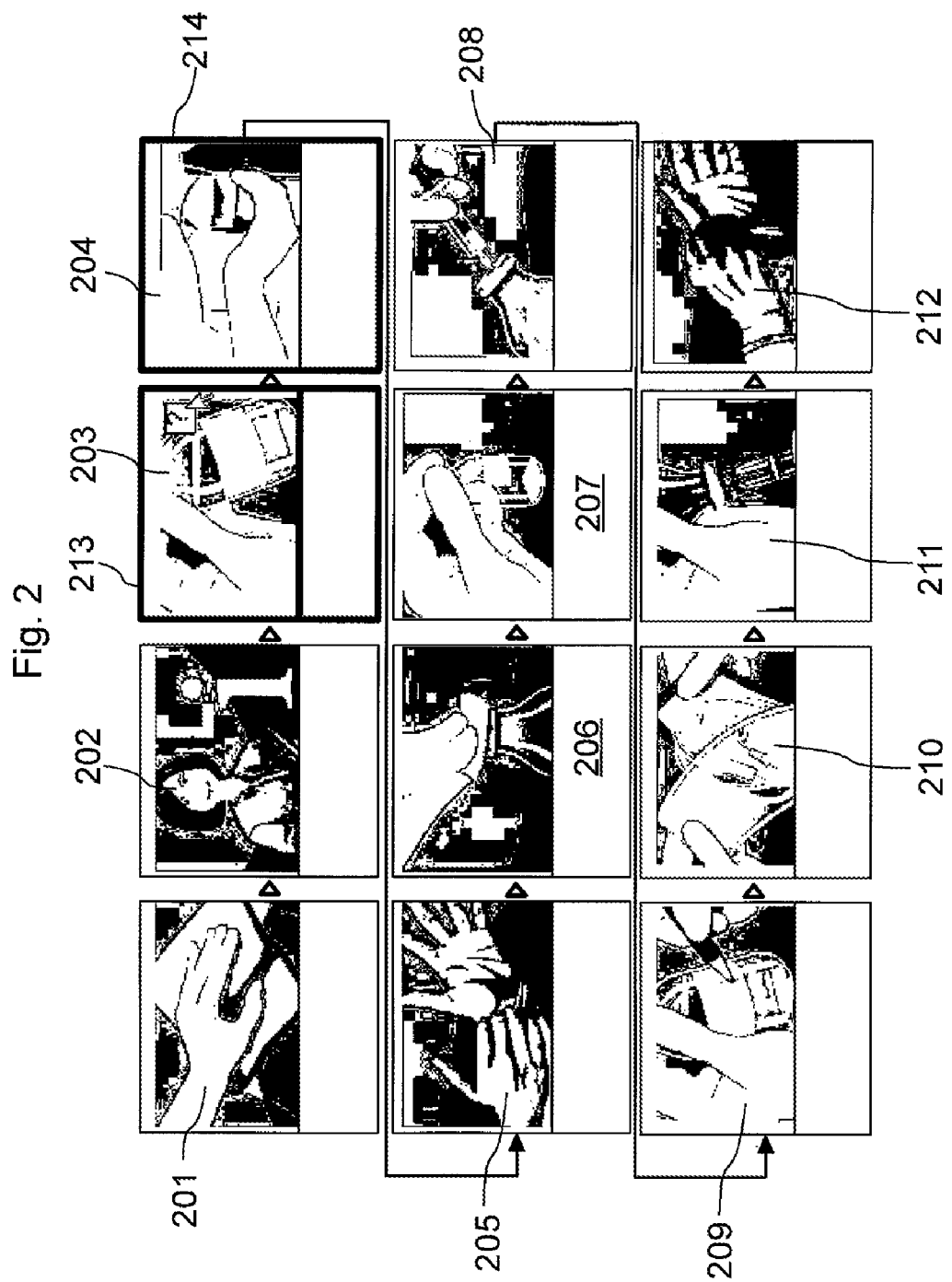

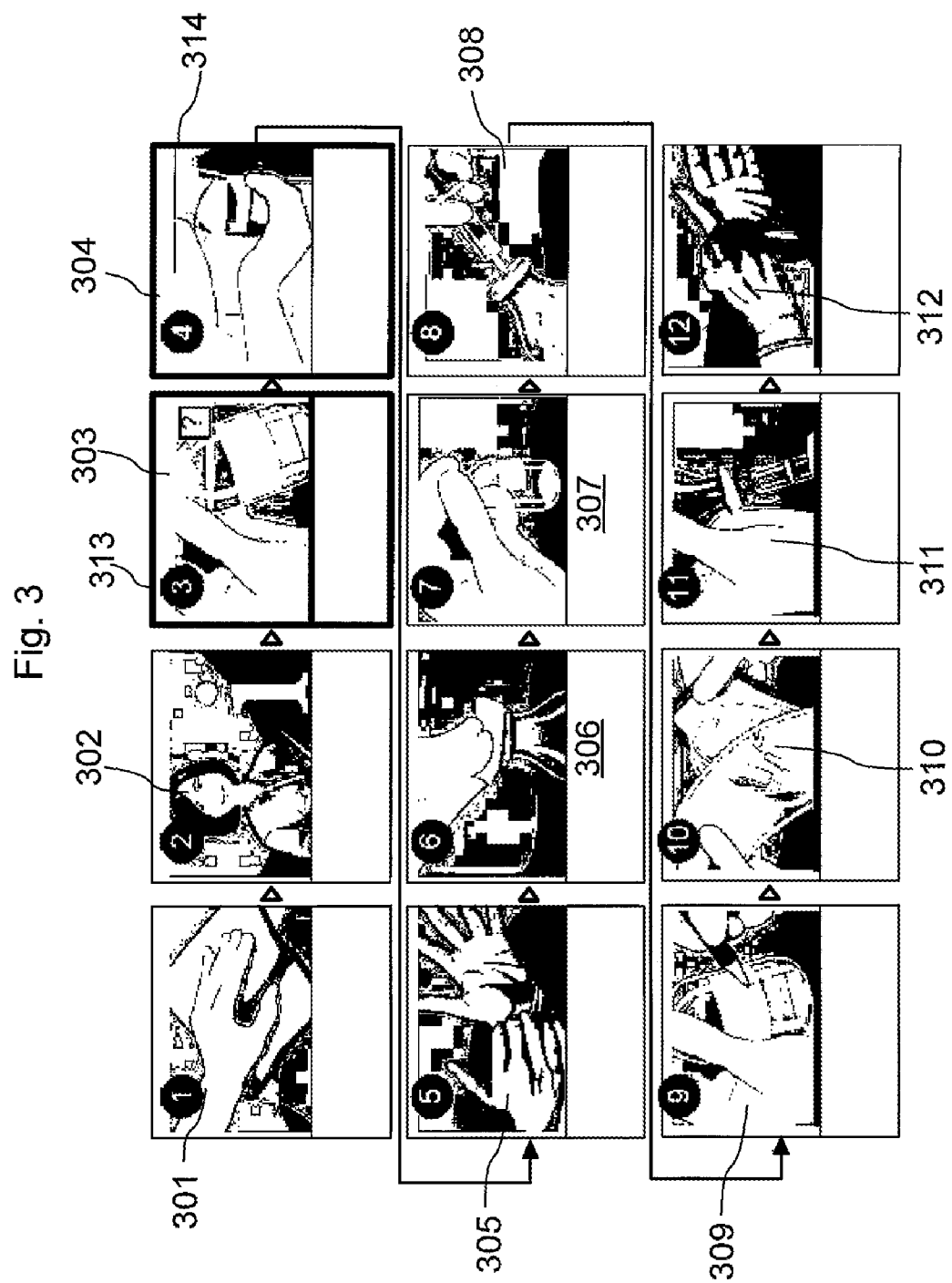

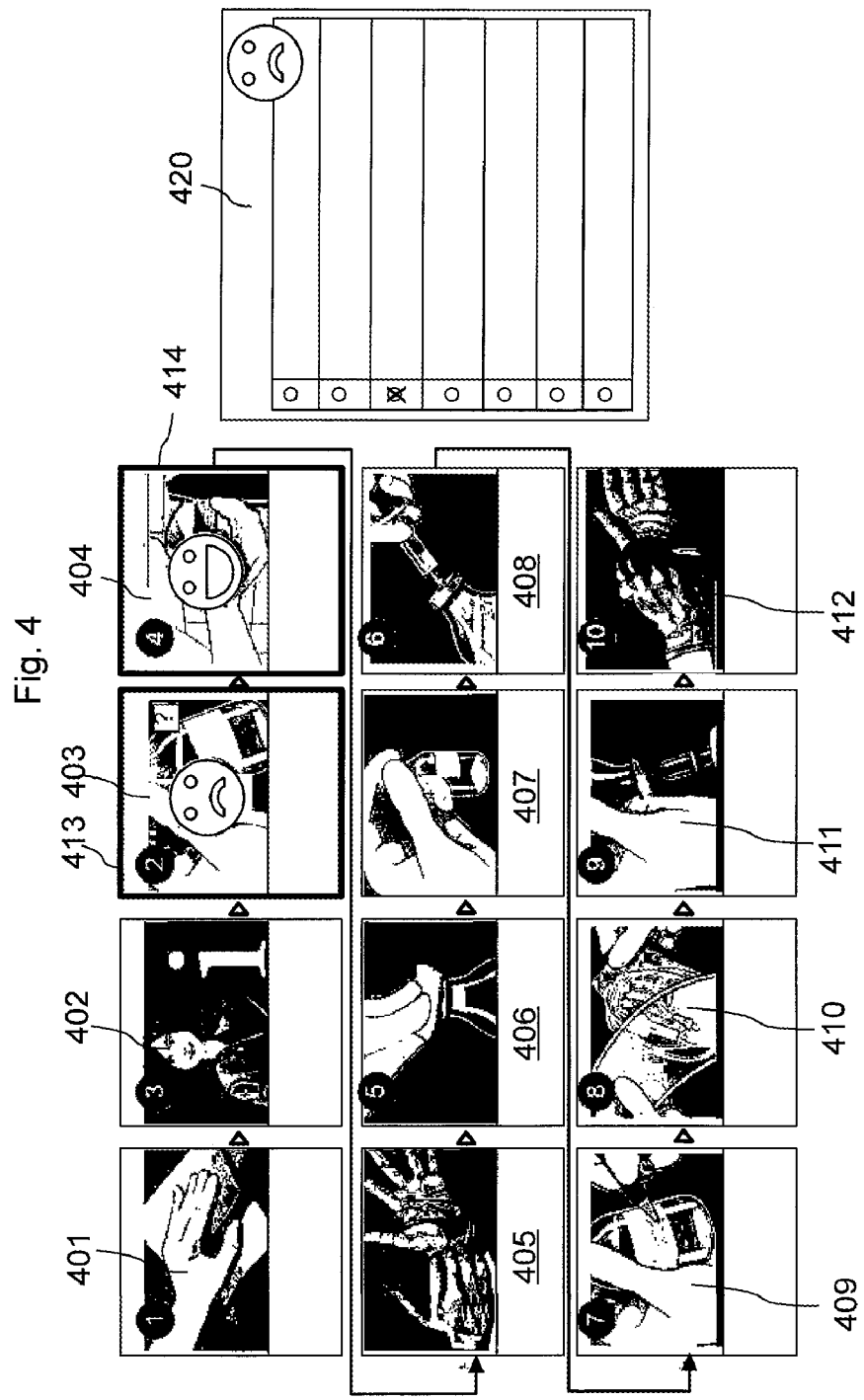

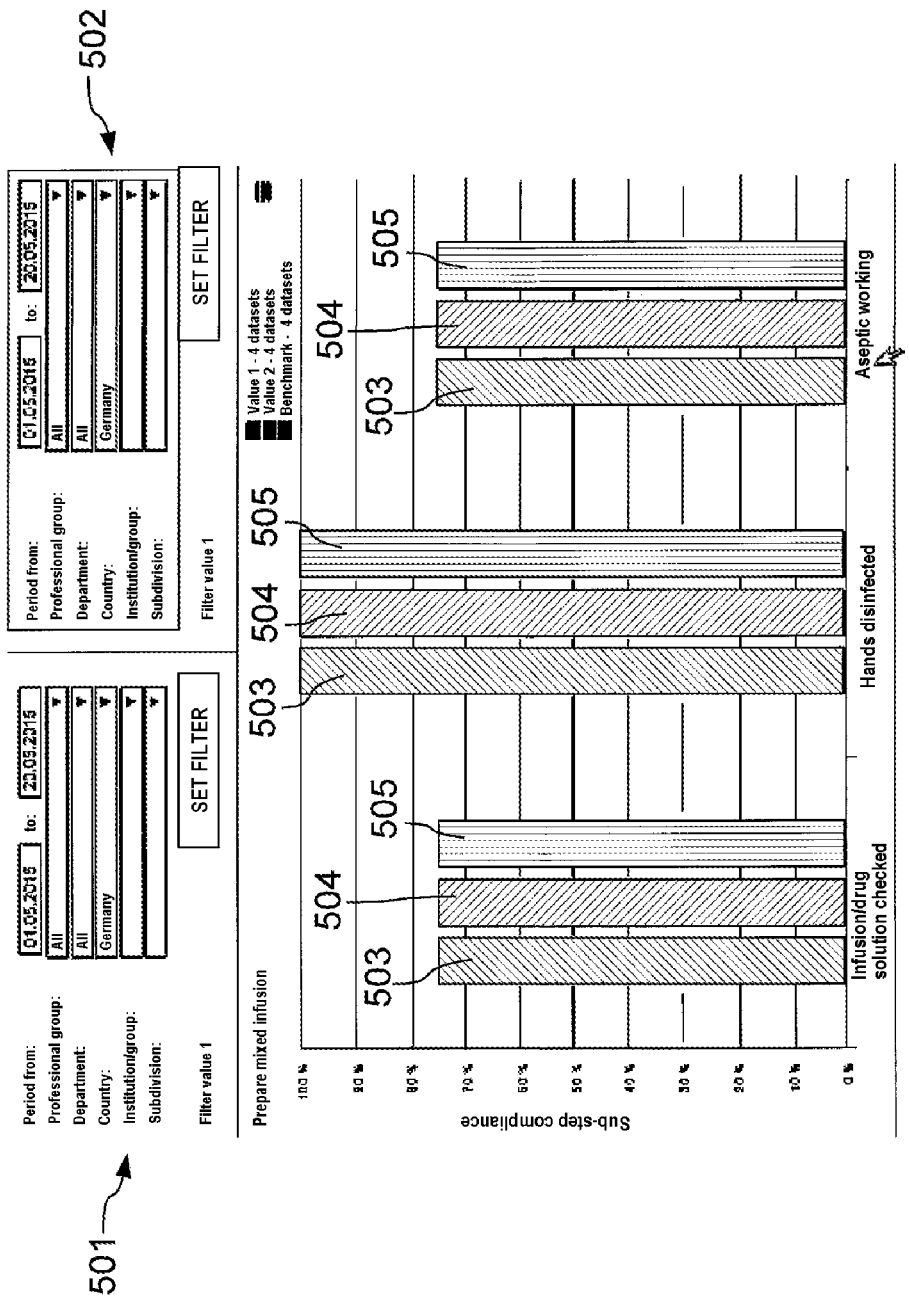

CARE SUPPORT DEVICE AND METHOD FOR CARE SUPPORT

This application claims priority to German Patent Application No. 102015212454.1 filed on Jul. 2, 2015.

The invention relates to a care support device and a method for care support.

Compliance with hygiene standards is essential in patient care, particularly in the performance of invasive or minimal-invasive measures or in treatments intended for wound care or intravenous administration of drugs or the preparation thereof. Working procedures which in each case indicate necessary hygiene measures in the correct sequence must therefore be regularly observed by professional staff.

In addition, individual work steps may have differing degrees of importance in relation to care. For example, infection-related steps which are essential with a focus on patient protection and the avoidance of healthcare-associated infections (HAI) are set out in corresponding instructions or recommendations. Recommendations of this type are published, for example, by the World Health Organization (WHO), a Center for Disease Control (CDC) or the Robert Koch Institute (RKI).

These recommendations are indicated, for example, in categories in a guideline for hospital hygiene and infection prevention. Categories I A, I B, etc., are known, which are published in their current version, for example by the RKI or a CDC.

These recommendations must be observed in working procedures in the provision of care. They may also be published, for example, in textbooks. The aim thereof is to guarantee optimum patient care.

Nursing staff are given corresponding training and further training in order to guarantee this.

However, in the case of complex working procedures, the problem arises that working practices change due to new scientific findings or new medical equipment or resources. Work steps which form an integral part of a working procedure must, for example, be replaced as a result, or must be performed at a different stage of the working procedure or with different resources.

The correct performance of the working procedures can be documented or checked by observers in hospitals in order to guarantee quality standards.

An observer is increasingly faced with the challenge of detecting the correct performance of the complex working procedures in real time. To do this, the observer must detect, evaluate or assess a multiplicity of changing complex working procedures at the same, in some instances very high, speed at which the individual work steps have to be performed.

Consulting a textbook or a plurality of textbooks is out of the question here for time reasons, since the sequence of the work steps in relation to one another, the severity of the consequences of an incorrect sequence or the omission of a work step due to the complexity and changing working procedures is therefore not possible in real time.

The object of the present invention is to produce a care support device and a method for care support which eliminates the existing restrictions in the observation of working procedures in care.

This object is achieved by the care support device, by providing:

an image output device which is configured to display symbols which visualize a care procedure, a specification device which is configured to specify symbols which are to be displayed based on a target care procedure, a detection device which is configured to detect a user input and assign displayed symbols to an actual care procedure based on the user input, an image generation device which is configured to generate symbols which visualize the actual care procedure, wherein the image output device can simultaneously display symbols which visualize the target care procedure and symbols which visualize the actual care procedure.

This object is achieved with the method for care support by:

displaying symbols which visualize a care procedure on an image output device, specifying symbols which are to be displayed based on a target care procedure, detecting a user input, assigning displayed symbols to an actual care procedure based on the user input, generating symbols which visualize the actual care procedure, wherein symbols which visualize the target care procedure and symbols which visualize the actual care procedure are displayed simultaneously on the image output device.

The perception and cognizance of information in real time is thereby enabled for the human observer who appropriately designs the detection, evaluation or assessment of the care procedure in real time or first enables it for specific, in particular complex, working procedures.

Further details, features and advantages of the invention can be found in the attached patent claims and in the graphical representation and the following description of preferred embodiments of the invention. In the drawing:

FIG. 2 shows schematically a representation of a target care procedure;

FIG. 3 shows schematically a representation of an actual care procedure;

FIG. 4 shows schematically a representation of a target care procedure and an actual care procedure simultaneously, alongside one another;

FIG. 5 shows schematically a user interface.

FIG. 1 shows a care support device 100.

Figure 1:
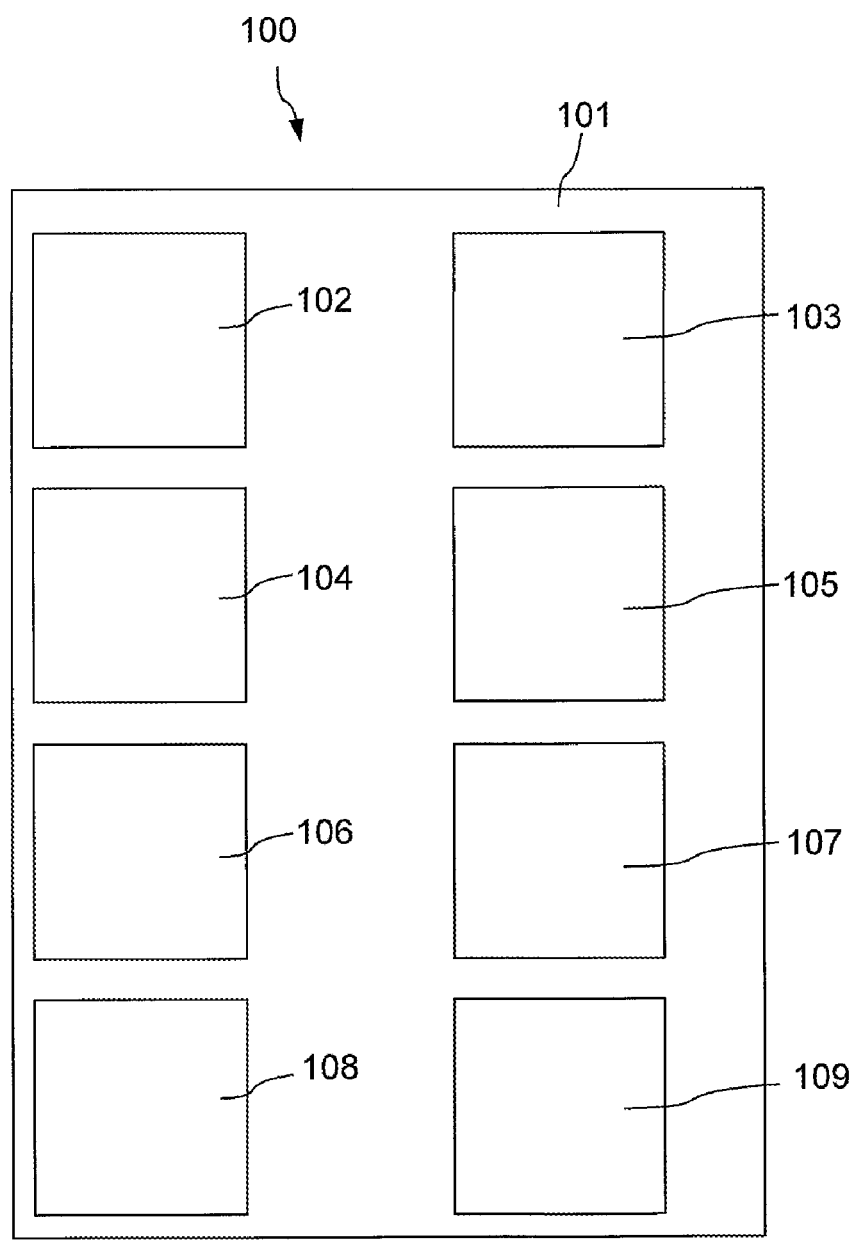
FIG. 1 shows schematically a part of an embodiment of the device according to the invention.

The care support device 100 is, for example, a portable flat computer.

The care support device 100 has an image output device 102. The image output device 102 is configured to display symbols which visualize a care procedure. In the example, the image output device 102 has a touch-sensitive screen 101 to display the symbols. The image output device 102 comprises, for example, a graphics card (not shown) by which the screen 101 is controlled to output the symbols.

The care support device 100 has a specification device 103 which is configured to specify symbols which are to be displayed based on a target care procedure. In the example, the symbols are specified for the image output device 102 and are output by the latter in an area on the touch-sensitive screen 101 defined by the sequence of the specification. In the example, a symbol which visualizes the respective work step of a care procedure is disposed for this purpose in the defined area in which the respective symbol is displayed.

An output of symbols 201-212 of a target care procedure of this type by the image output device 102 is shown schematically in FIG. 2. The first sequence of the specification and the sequence of the reproduction match one another in the example. The sequence is shown by small arrows starting with the symbol 201. This simplifies the perception of the target care procedure.

It is preferably provided to highlight particularly important steps with a border. For example, the symbol 203 is shown with a first border 213. The symbol 204 is shown, for example, with a second border 214. The borders preferably differ from one another in terms of their shape or color.

The care support device 100 has a detection device 104 which is configured to detect a user input and assign displayed symbols to an actual care procedure based on the user input. In the example, the detection device 104 interworks with the touch-sensitive screen 101. The detection device 104 recognizes a touch of the user and its position on the screen 101. The detection device 104 assigns the recognized position to the actual care procedure, for example by adding a new position behind in a second sequence of the actual care procedure. This means that, by means of the second sequence, the symbol which is displayed in the defined area which overlaps with the recognized position is assigned to the actual care procedure in the second sequence. This means that the respective work step assigned to the symbol is assigned to the actual care procedure.

The care support device 100 furthermore has an image generation device 105 which is configured to generate symbols which visualize the actual care procedure. In the example, in addition to a symbol which visualizes the respective work step of a care procedure, information relating to the second sequence is disposed for this purpose in the area in which the respective symbol is displayed.

For this purpose, the image generation device 105 is configured to overlay a specified symbol which is assigned to the actual care procedure on at least one displayed symbol which is assigned to the target care procedure based on the detected user input.

For example, the symbols which visualize the respective work steps of the care procedure are overlaid with the respective information relating to the sequence in the area in which the respective symbol is displayed.

Alternatively, the symbol representing the work step of the target care procedure can be replaced with a symbol representing the actual care procedure. For this purpose, in addition to the symbols representing the work steps of the target care procedure, further symbols can be provided which represent the identical work step and have the information relating to the second sequence.

An output of symbols 301-312 of an actual care procedure by the image output device 102 is shown schematically in FIG. 3. The first sequence of the target care procedure and the second sequence of the actual care procedure match one another in the example. The second sequence is shown in the example by small numbers in circles, starting with the number 1 for the symbol 301 and ending with the number 12 for the symbol 312. In the example, these numbers are disposed in a corner of the respective symbol. This simplifies the perception of the actual care procedure. Any symbols other than Arabic numerals, for example Roman numerals, can similarly be used. The position at which the number is displayed can also be located in a different part of the defined area of the respective work step, for example in the middle.

It is preferably provided to highlight particularly important steps with a border. For example, the symbol 303 is shown with a first border 313. The symbol 312 is shown, for example, with a second border 314. The representation of the border is preferably specified according to the representation of the border for the symbol of the target care procedure.

The care support device 100 furthermore has a comparison device 106 which is configured to compare the first sequence in which the symbols to be displayed are specified based on the target care procedure with the second sequence in which user inputs for the displayed symbols have been detected. To do this, for example, for each position from the second sequence detected during a user input, the symbol in the first sequence which has been displayed at this position is searched for. To do this, a check is carried out, for example, to determine whether the defined area at which the symbol has been displayed overlaps with the position. A check is then carried out to determine whether the respective entries are located at the same position in the respective sequence.

The image output device 105 is designed to display simultaneously symbols which visualize the target care procedure and symbols which visualize the actual care procedure.

Symbols which visualize individual work steps are stored, for example, in a memory (not shown) in the care support device 100. These symbols are read, for example, from the memory and are specified in the corresponding first sequence.

The care support device 100 preferably has an evaluation device 107 which is configured to specify a spontaneous assessment. To do this, the evaluation device 107 generates, for example, information relating to the evaluation depending on the result of the comparison of the first sequence of the target care procedure with the second sequence of the actual care procedure. In the example, emoticons, in particular the schematic representation of a happy, neutral or sad face, is used as the spontaneous evaluation. These can preferably be colored using the colors green, amber or red.

If the positions of a work step match one another in the two sequences, a green or happy face, for example, is specified as the spontaneous evaluation.

Otherwise, a red or sad face, for example, is specified as the spontaneous evaluation.

In the event of a match or absence of a match in the positions of a work step in the two sequences, the evaluation device 107 can be designed to take account of a further differentiation for the spontaneous evaluation. For example, either a red or sad face, or an amber or neutral face, is displayed depending on the importance of the work step for hygiene. For example, the categories, in particular I A or I B, of the RKI or of a CDC, are used for this differentiation. Alternatively or additionally, it is also conceivable to use further categories of work steps (Z, Y, X, . . . ) relating to infection protection for this differentiation.

A spontaneous evaluation for work steps which are assigned to a category of this type is preferably displayed.

The image output device 105 can display the spontaneous evaluation simultaneously with the symbols which visualize the target care procedure and the actual care procedure.

The image output device 105 is preferably configured to display the specified spontaneous evaluation adjacent to the respective assigned symbol or overlaid on the respective assigned symbol.

The care support device 100 furthermore optionally has an input device 108 which is configured to specify an input dialogue based on the detected user input, wherein the image output device 105 can display the input dialogue simultaneously with, in particular adjacent to, the symbols which visualize the target care procedure and the actual care procedure. This input dialogue comprises, for example, comments or notes on a work step. The assignment is performed, for example, by means of a list provided for the respective work step containing the specified comments or notes. These comments or notes are stored, for example, in the input device 108. They may be displayed, for example, as a list or checklist in the input dialogue.

The input dialogue comprises, for example, an assigned selection button for each selectable comment or note. A user input, for example a touch on the touch-sensitive screen 101 in the area of the display of the selection button, is detected by the input device 108 and is interpreted as a selection of the respective comment or note. The respective comment or note is stored, for example, together with information relating to the work step to which the input dialogue is assigned.

An output of symbols 401-412 of an actual care procedure by the image output device 102 is shown schematically in FIG. 4. The first sequence of the target care procedure and the second sequence of the actual care procedure do not match one another in the example. The sequence of the user input is described in the example as for FIG. 3 by small numbers displayed in circles. The user input results in the comparison of the first sequence with the second sequence indicated in Table 1. In Table 1, the first sequence is reproduced by the numbering of the symbols of the work steps in FIG. 4. The second sequence is reproduced with the numbers in the circle shown in FIG. 4. Other assignments, for example by names, are similarly possible.

For example, the work steps are explained by a title which is shown below the graphic symbols. In the example, a "prepare mixed fusion" working procedure is represented symbolically. Furthermore, the following can be displayed under the symbols in FIGS. 2 to 4:

201, 301, 401: Work surface wiped with disinfectant
202, 302, 402: Materials put together
203, 303, 403: Infusion/drug solution checked
204, 304, 404: Hands disinfected
205, 305, 405: Antibiotics, cytostatics: gloves put on
208, 306, 406: Rubber membranes of bottles disinfected
207, 307, 407: Drugs dissolved
208, 308, 408: Drugs added to infusion solution
209, 309, 409: Infusion bottle labelled
210, 310, 410: Infusion system unpacked
211, 311, 411: Infusion system connected to infusion bottle
212, 312, 412: Where appropriate, gloves removed It is preferably provided to highlight particularly important steps with a border. The symbol 403 is shown, for example, with a first border 413. The symbol 404 is shown, for example, with a second border 414. The same representation of the borders as specified for the representation of the target care procedure also is preferably used.

The representation of one of the previously described borders is selected, for example, based on WHO, RKI or CDC recommendations, depending on the category. The border representation for category I A, for example, is specified differently from the representation for category I B. Symbols which do not correspond to any category are presented without a border in the example. As a difference, for example, a border of a category I A symbol is presented as thicker or red. The border of a category I B symbol, for example, is presented as thinner or amber.

However, it may also be advantageous to highlight the symbols of categories I A and I B or further categories (Z, Y, X, etc.,) in a similar manner, for example in each case with a thick or red border.

The information relating to the target care procedure and actual care procedure and the additional information described for the category or input dialogue is set out in Table 1 below. This table can be created, stored and modified, for example, in the care support device.

TABLE 1

| First sequence | Second sequence | Category | Input dialogue |
|---|---|---|---|
| 401 | 1 | — | |
| 402 | 3 | — | |
| 403 | 2 | Z | Comment 1 |
| 404 | 4 | Y | |
| 405 | — | — | |
| 406 | 5 | — | |
| 407 | — | — | |
| 408 | 6 | — | |
| 409 | 7 | — | |
| 410 | 8 | — | |
| 411 | 9 | — | |
| 412 | 10 | — | |

According to the result of the comparison of the sequences, the sequence of steps 2 and 3 has been transposed. This becomes immediately evident to the observer through the indication of the numbers in the circle in the area of the display of the work steps concerned. The spontaneous evaluation is shown in FIG. 4 in the area of the display of the symbols 403 and 404. The symbols relate to work steps which are assigned to the categories of work steps Z, Y relating to infection protection. Work steps of the first sequence not contained in the second sequence are given no numbering in the example. It thereby becomes evident which work steps have not been carried out. The target care procedure and the actual care procedure are thus presented simultaneously alongside one another. This simplifies the perception of the actual care procedure and the differences between the target care procedure and the actual care procedure.

An input dialogue 420 is furthermore displayed based on the comparison result. In the example, the input dialogue 420 enables a comment 1 to be entered for the work step which has been presented as the symbol 403. The input dialogue is output, for example, when the work step for the second sequence is added. The input dialogue is output, for example, when a user input is recognized by means of which the symbol representing this work step is selected.

The comment 1 is selected, for example, from the list of specified comments as described.

In the example, an aseptic dialogue is displayed, consisting of the following points:
  membrane has been touched following disinfection
  metal mandrel of cannula has been touched,
  the syringe opening has been touched,
  the same syringe has been used for dissolving and adding drugs,
  membrane has been pierced with already used cannula,
  the infusion system spike has been touched,
  syringe, cannula, infusion system were not sterile.

A recognized user input is stored, for example in the form of the text of the list as a comment in Table 1. This is done, for example, as soon as at least one entry has been selected from the list. Additional sub-steps of a work step become observable and detectable as a result.

A question with a list of answers can also be output instead of the list indicated above. The answer(s) is/are then stored, for example, as a comment.

The assignment of the work steps to the categories, for example in Table 1, is particularly preferably specified in such a way that the user cannot himself define the categories.

The care support device 100 is particularly preferably designed to display the spontaneous evaluation information relating to the sequence within a defined time period following a recognized user input. The time period is, for example, 1 millisecond to 10 seconds, preferably 1 millisecond to 5 seconds, 1 millisecond to 1 second, in particular less than 100 milliseconds. A separate symbol can also be provided to trigger the evaluation. An evaluation of all work steps is then triggered only after the detection of a user input by means of which this symbol has been selected.

The care support device 100 can optionally comprise a communication interface 109 which is configured to transmit information relating to the actual care procedure, in particular addressed to a server. This process can be triggered by the selection of a corresponding symbol.

The server is designed, for example, to receive the information from a plurality of care support devices 100.

It is particularly preferable to display the information relating to the spontaneous evaluation or the actual care procedure in such a way that a screen view is not storable.

For example, the information indicated in Table 1 is transmitted by means of an Internet connection. An Internet Protocol/Transmission Control Protocol connection, for example, is set up between the care support device 100 and the server for this purpose. The information is transmitted, for example, by means of the Hypertext Transfer Protocol or the Hypertext Transfer Protocol Secure.

According to a first variant, the information transmitted to the server comprises all information relating to the actual care procedure. However, it is provided, in particular, that the information transmitted to the server comprises only an extract, i.e. a subset, of the information relating to the actual care procedure. The information transmitted to the server thus contains, in particular, information relating to the work steps which are assigned to the categories of work steps relating to infection protection. It can preferably be provided that the information transmitted to the server comprises, in particular, no information relating to the work steps which are not assigned to any category of work steps relating to infection protection.

In the example, the care support device 100 is represented as a tablet computer. The individual components previously described are contained therein. The care support device 100 has, for example, one or more microprocessors which can execute a program code which performs the method described below when the program code runs on the tablet. The program code is stored, for example, in a memory (not shown) in the tablet.

The care support devices 100 transmit, for example, a unique identification, e.g. their Internet Protocol address or a name, to the server in order to enable an assignment of the transmitted data to the respective care support device 100. The name is, for example, the name of the ward in a specific hospital or the name of the hospital which uses the respective care support device 100. The server retains this assignment or generates an assignment by means of the unique identification.

This information relating to the care support device 100 is stored, for example, in the care support device 100. The care support device 100 preferably comprises a graphical user interface by means of which the name can be entered before the start of the observation.

The information relating to a plurality of observations, for example from a plurality of tables which are received from a specific care support device 100 is consolidated. This means that a mean value, for example, is stored for the result of the comparison of the sequences for a specific working procedure. Alternatively or additionally, a standard deviation or a percentage indication of the recognized deviations or matches can also be used.

The consolidation can also take place in the care support device 100 before the transmission. In this case, for example, tables which are structured in the same way as Table 1, resulting from a plurality of observations, a consolidated table which is structured in the same way as Table 1 is generated and transmitted.

The server is designed to present the data from the tables of different care support devices 100 or different hospitals alongside one another. A corresponding interface 500 is shown in FIG. 5.

A first input screen 501, for example, is provided for the selection of a first ward or a first hospital. A second input screen 502, for example, is provided for the selection of a second ward or a second hospital.

The comparison results, for example, of the wards or hospitals selected in the input screen are shown in a first bar 503 and a second bar 504 for a specified or selectable working procedure or a specified or selectable work step. A comparison with a comparative value 505 can furthermore be provided.

A method for care support is described below with reference to the illustrations in FIG. 4. The method starts, for example, when a program code, for example an application on the tablet, is started.

Following the start, a first start-up screen is optionally displayed. The first start-up screen provides a user interface. The user interface enables, for example, the selection of a name for the ward or the hospital of the observer or the selection of a working procedure to be observed or a professional group.

This information is used, for example, to create a dataset comprising the entered information. In the example, the dataset is assigned to a table which is structured in the same way as the described Table 1.

In the next step, symbols to be displayed are specified based on a specified or the selected target care procedure. The symbols are specified, for example, in the first sequence.

The symbols which visualize the selected target care procedure are then displayed on the image output device 102. The symbols are displayed, for example, in the first sequence.

A user input is then detected. The position of the user input on the touch-sensitive screen, for example, is detected for this purpose.

In the following step, a displayed symbol is assigned to the actual care procedure based on the user input. The detected position, for example, is appended to the second sequence.

A symbol which visualizes the actual care procedure is then generated. The number to be displayed, for example, is determined by means of the point at which the detected position is located in the second sequence.

In a further step, the first sequence is preferably compared with the second sequence.

The symbol which visualizes the actual care procedure is visualized on the image output device simultaneously with at least one symbol which visualizes the target care procedure.

To do this, based on the detected user input, at least one displayed symbol which is assigned to the target care procedure is preferably replaced or overlaid with at least one specified symbol which is assigned to the actual care procedure.

Particularly if this is provided for the respective work step, the input dialogue is preferably specified based on the detected user input and is displayed simultaneously with, in particular adjacent to, the symbols which visualize the target care procedure and the actual care procedure.

The simultaneous display preferably takes place within the specific time period following the recognized user input.

Particularly if this is provided for the respective work step, the spontaneous evaluation is preferably specified and displayed simultaneously with the symbols which visualize the target care procedure and the actual care procedure.

The specified spontaneous evaluation is preferably assigned to a specific displayed symbol and is displayed adjacent to the respective assigned symbol or overlaid on the respective assigned symbol.

These steps are preferably repeated, in particular until a user input is recognized which signals the completion of the observation. As a result, the actual care procedure is displayed simultaneously and, in particular, alongside the target care procedure.

Information relating to the actual care procedure can optionally be transmitted, in particular addressed to the server. This is done, in particular, in response to the recognition of a corresponding user input which requests the transmission. Alternatively, the transmission can take place as soon as a connection is set up to the server. The information is preferably transmitted via the communication interface.

According to a first variant, the information transmitted to the server comprises all information relating to the actual care procedure. However, it is provided, in particular, that only an extract, i.e. a subset, of the information relating to the actual care procedure is transmitted to the server. Thus, in particular, information relating to the work steps which are assigned to the category of work steps relating to infection protection is transmitted to the server. It can preferably be provided not to transmit any information to the server relating to the work steps which are not assigned to any category.

The server preferably has a receiving device to receive the information relating to the actual care procedure. The receiving device can be designed to assign the received information to a transmitting care support device 100.

The server furthermore has a data processing device to evaluate the received information, in particular taking account of the identification of the transmitting care support device 100.

The data processing device is preferably designed to consolidate the information relating to the actual care procedure which has been gathered by one or various care support devices 100 in different observation processes.

The server furthermore has a storage device to store the received information or the result of the evaluation. The storage device may also be disposed outside the server.

The server furthermore has a man-machine interface, for example a monitor and a computer mouse. Alternatively or additionally, the server is connected to a terminal which has a man-machine interface.

The interface 500 can be operated and displayed by the man-machine interface.

It is particularly advantageous to configure the server and the care support device 100 in such a way that a communication or the transmission of the information can take place, in particular, without further user inputs or automatically.

For this purpose, the connection for the data transmission can be set up, for example, directly between the server and the care support device 100 or indirectly, for example via a communication network or a plurality of communication networks. The connection may be wireless, wired or both.

In one variant, the care support device 100 and the server form a system for care support. This system is particularly simple to operate.

According to a further variant, the system comprises a plurality of care support devices 100. The system may also comprise a plurality of servers or terminals.

The invention claimed is:

1. A care support device, comprising:
an image output device configured to display symbols which visualize a care procedure,
a specification device configured to specify symbols which are to be displayed based on a target care procedure,
a detection device configured to detect a hospital user input and assign displayed symbols to an actual care procedure based on the hospital user input,
an image generation device configured to generate symbols which visualize the actual care procedure,
wherein the image output device simultaneously displays symbols which visualize the target care procedure and symbols which visualize the actual care procedure, and
a comparison device which is configured to compare a first sequence in which symbols to be displayed are specified based on the target care procedure with a second sequence in which the hospital user inputs for displayed symbols which are assigned to the actual care procedure have been detected,
an evaluation device which is configured to generate a spontaneous evaluation depending on the result of the comparison of the first sequence of the target care procedure with the second sequence of the actual care procedure and which in the absence of a match in the positions of a work step of the care procedure is configured to assign the spontaneous evaluation to a specific displayed symbol,
wherein the image output device is configured to display the spontaneous evaluation simultaneously with the symbols which visualize the target care procedure and the actual care procedure.

2. The care support device of claim 1 further comprising an input device which is configured to specify an input dialogue based on the detected user input, wherein the image output device is configured to display the input dialogue simultaneously with the symbols which visualize the target care procedure and the actual care procedure.

3. The care support of claim 1 further comprising a communication interface (109) which is configured to transmit information relating to the actual care procedure.

4. A method for care support comprising
displaying on an image output device, symbols which visualize a care procedure,
specifying with a specification device, symbols to be displayed on the image output device based on a target care procedure,
detecting with a detection device a hospital user input,
assigning with the detection device displayed symbols to an actual care procedure based on the user input to the detection device,
generating with an image generation device, symbols which visualize the actual care procedure,
wherein symbols which visualize the target care procedure and symbols which visualize the actual care procedure are displayed simultaneously on the image output device, and evaluating with an evaluation device a spontaneous evaluation which occurs in the absence of a match in the positions of a work step of the care procedure and which assigns the specified spontaneous evaluation to a specific displayed symbol, which specific displayed symbol is displayed simultaneously with the symbols which visualize the target care procedure and the actual care procedure either adjacent to the respective assigned symbol or overlaid on the respective assigned symbol.

5. The method of claim 4 further comprising:
specifying an input dialogue with an input device based on the detected hospital user input, and
displaying, on the image output device, the input dialogue simultaneously with the symbols which visualize the target care procedure and the actual care procedure.

6. The method of claim 4 further comprising a communication interface for transmitting information relating to the actual care procedure.

7. A system for care support, comprising at least one care support device as claimed in claim 3, wherein the communication interface is configured to transmit information relating to the actual care produced to a server, wherein the server has a receiving device for receiving the information, and a man-machine interface for displaying the information.

8. The care support device of claim 2 wherein the display of the input dialogue is adjacent to the symbols which visualize the target care procedure and the actual care procedure.

9. The care support device of claim 3 wherein the communication interface is configured to transmit information relating to the actual care procedure, to a server.

10. The method of claim 5 wherein the input dialogue is displayed adjacent to, the symbols which visualize the target care procedure and the actual care procedure.

11. The method of claim 6 wherein the communication interface for transmitting information relating to the actual care procedure is addressed to a server.

12. The system for care support of claim 7, wherein the man-machine interface for displaying the information is on an interface.

13. The care support device of claim 1, wherein the hospital user is a nurse.

* * * * *